United States Patent [19]

Bertoglio-Matte

[11] Patent Number: 4,568,649
[45] Date of Patent: Feb. 4, 1986

[54] IMMEDIATE LIGAND DETECTION ASSAY

[75] Inventor: Jacques H. Bertoglio-Matte, Seattle, Wash.

[73] Assignee: Immunex Corporation, Seattle, Wash.

[21] Appl. No.: 468,558

[22] Filed: Feb. 22, 1983

[51] Int. Cl.[4] .................... G01N 33/52; G01N 33/54; G01N 33/58

[52] U.S. Cl. .................................. 436/534; 436/537; 436/800; 436/804; 436/815; 436/817; 436/824

[58] Field of Search ............... 436/508, 531, 534, 537, 436/800, 808, 824, 828

[56] References Cited

U.S. PATENT DOCUMENTS

| 4,000,252 | 12/1976 | Kosak | 436/531 |
|---|---|---|---|
| 4,108,972 | 8/1978 | Dreyer | 436/531 |
| 4,161,515 | 7/1979 | Ullman | 436/531 |
| 4,271,139 | 6/1981 | Hart | 436/531 |

OTHER PUBLICATIONS

Virtanen et al., Chemical Abstracts, 93 (1980) #230464d.
Lehtola et al., Chemical Abstracts, 97 (1982) #203286y.
Wurzburger et al, J. Pharmacol. Exp. Therapeuti., vol. 203 (1977) 435–41.
Hart and Greenwald, "Scintillation Proximity Assay (SPA)—A New Method of Immunoassay", *Molecular Immunology*, 265 (1979).
Hart and Greenwald, "Scintillation–Proximity Assay of Antigen–Antibody Binding Kinetics: Concice Communication", 20, *Journal of Nuclear Medicine*, 1062 (1979).

*Primary Examiner*—Christine M. Nucker
*Attorney, Agent, or Firm*—Christensen, O'Connor, Johnson & Kindness

[57] ABSTRACT

A test kit and assay for detecting the presence of minute amounts of an organic reactant in a test sample includes a plurality of beads or other types of support structures that are impregnated with a fluorescer and coated with a ligand that specifically binds to the organic reactant being investigated. The beads are placed in an aqueous solution, together with the reactant which has been radiolabeled. The portion of the radiolabeled reactant that binds to the ligand is thereby brought in close enough proximity to the beads to activate the fluorescer to produce light energy. The radiolabeled reactant that does not bind to the ligand is, for the most part, disposed too far away from the beads to enable the radioactive energy emitted thereby to reach the fluorescer integrated into the beads. Thus, the level of light energy produced by the fluorescer is indicative of the amount of reactant present in the test sample.

15 Claims, 2 Drawing Figures

IMMEDIATE LIGAND DETECTION ASSAY

TECHNICAL FIELD

The present invention relates to an assay for detecting the presence of small amounts of organic material, and more particularly to an assay to detect the presence of organic materials by monitoring the light energy produced when radioactive organic molecules of interest biochemically and specifically bind to a binding structure.

BACKGROUND OF THE INVENTION

In clinical applications, in research and in industry, a need exists to detect the presence of minute amounts of organic material, such as antigens, antibodies, hormones, metabolites, enzymes, and drugs. In clinical situations, detecting the presence or absence of metabolites, hormones, or other organic factors in serum or in other body fluids may be useful in the diagnosis of many clinical conditions, such as pregnancy, infection, blood disorders, hepatitis, etc. The detection and quantitative analysis of organic agents is often required in immunological, biological, chemical, or other types of scientific and medical research. In industry, assays for organic materials are utilized in quality control procedures for the production of chemicals and in monitoring the pollution of water.

Of the numerous chemical and biological assays that have been developed to detect organic materials, of relevance to the present invention are precipitation and agglutination assays. In a typical precipitation assay, the organic material interacts with a reactant to form a complex that falls out of solution. In agglutination reactions, the organic substance of interest cross-links an insoluble reactant to cause the reactant to flocculate. Optical scattering techniques are commonly used to measure the flocculation. A drawback of precipitation and agglutination assays is that they are not as sensitive as radioimmunoassays. Also, although optical techniques have been developed to improve the sensitivity of these assays, these techniques require specialized equipment and analysis.

Another type of known assay for organic materials involves labeling either the organic material or a reactant thereto with a radioactive, fluorescent or other type of tracer substance to ascertain the extent to which the organic material has coupled with its reactant.

Radioimmunoassay is one of the most common types of these "tracer" assays. Radioimmunoassay involves combining a known amount of radiolabeled organic material with a sample containing an unknown amount of unlabeled organic material of interest together with a specific antibody that binds indiscriminantly to the labeled and unlabeled organic materials to form a complex. After an incubation period, the unbound organic materials are separated from the bound organic materials, typically by precipitation of the complex with polyethylene glycol, adsorption of the unbound material with activated charcoal or utilization of solid-phase reagents. Then the radioactivity of either of these two fractions is measured. A certain amount of the labeled and unlabeled organic material will be bound to the reactant, with the amount of the bound labeled organic material being inversely related to the quantity of unlabeled inorganic material present in the sample being tested.

A drawback of the radioimmunoassay is that the procedures for separating the bound organic materials from the unbound require a significant number of time-consuming operations that are often complicated and expensive. The separation procedures involve repeatedly washing the complex of organic material and antibody with a rinsing solution and/or centrifuging the mixture to remove the unbound organic material from the reactant, thereby generating radioactive waste material with each washing. By the time that the separation process has been completed, significant volumes of radioactive waste material are produced. This waste material is not only expensive to dispose of, but also presents a potential health hazard to persons handling the material, including during the separation procedures.

In an assay utilizing fluorescence, the organic material may be labeled with an appropriate fluorescer, such as fluorescein isothiocyanate. The extent to which the fluorescer labeled organic materials bound to a specific reactant can be examined under a light microscope with a suitable light source and filters to provide incident light of the proper wavelength to cause fluorescence.

An example of a particular fluorescence technique is disclosed in U.S. Pat. No. 4,161,515 wherein an unknown organic compound, whose presence is being investigated, is mixed with: (1) a known quantity of antibody against the organic compound; (2) an organic analog, having a fluorescer bound thereto, which competes with the unknown organic compound for the antibody; and (3) an antibody for the fluorescer. The competition between the unknown organic material and the known analog-fluorescer effectively reduces the concentration of the antibody, thereby causing more of the fluorescer-antibody to combine with the analog-fluorescer. This, in turn, causes a corresponding change in the emission spectrum of the fluorescer.

A tracer assay that utilizes both fluorescence and radioactive substances is disclosed by U.S. Pat. No. 4,000,252 wherein a known quantity of radiolabeled antigen and a sample containing an unknown amount of unlabeled antigen are placed within an immunoscintillation cell. An insolubilized or solid phosphor, which is chemically or physically associated with an antibody to the antigens, is also added to the cell. The unbound antigens are washed from the cell and then the luminescence emitted by the phosphor due to activation from the radioactive energy from the found labeled antigens is measured inside a scintillation counter. Removal of the unbound antibodies from the cell requires several washing procedures that are not only time consuming, but also produce significant quantities of radioactive waste material.

Assays that combine tracer techniques with agglutination are disclosed by U.S. Pat. Nos. 4,018,972 and 4,271,139. In U.S. Pat. No. 4,108,972, microscopic carrier particles, each containing a fluorescent tracer material, and a biological reactant to the antibody or antigen being investigated, are placed in suspension. When the antigen or antibody is added to the suspension, it binds to the reactant coating to cause flocculation of the carrier particles. The flocculated material is then separated from the suspension fluid and other constituents by numerous washings. Thereafter, the flocculated material is dissolved and then assayed by flourescence techniques to determine the quantity of organic material present.

In U.S. Pat. No. 4,271,139, tritiated (radioactive) latex particles coated with antigen and polystyrene scintillant particles coated with the same antigen were placed in an aqueous medium with a sample containing an unknown quantity of a corresponding antibody. The number of tritiated antigen coated latex particles linked to the antigen coated scintillant particles is related to the concentration of antibody present. Also, when the two particles are linked together by the antibody, the radioactive energy from the tritiated particles initiates scintillation within the scintillant particles. Scintillations are then measured by an appropriate detector, with the detected level of scintillation being indicative of the quantity of antibody present. Addition of an unknown quantity of non-radioactive antigen then competes with the antigen coated bead binding to the antibody, thereby reducing bead agglutination, scintillation and signal. A drawback of this particular assay is that it requires both tritiated latex particles and polystyrene scintillant particles to be coated with antigen, which increases the expense and complexity of the assay. In addition, relative to the standard radioimmunoassay discussed above, extremely large suspension volumes are required for the assay to operate properly. The assay process of the '139 patent also requires the availability of relatively pure antigen to be used to bind to the two types of carrier particles. Relatively pure samples of antigen are both expensive and difficult to obtain.

Thus, it is a principal object of the present invention to provide an accurate, inexpensive, and rapid assay procedure and test kit for detecting the presence of extremely small amounts of organic materials.

A particular object of the present invention is to provide an assay of equivalent accuracy to present techniques, but which does not require highly skilled personnel or large amounts of time to perform using standard commercially available equipment.

A further particular, but highly important object of the present invention, is to provide an assay procedure that produces only a minimum volume of radioactive waste and requires only a minimum amount of handling of hazardous substances.

An additional particular object of the present invention is to provide an assay that can be used to rapidly test a large number of samples.

Another particular object of the present invention is to provide an assay that utilizes water as a suspension medium.

SUMMARY OF THE INVENTION

The foregoing and other objects are achieved in accordance with the present invention by providing a test kit and assay procedure which produces light energy at a level related to the amount of organic material present in a sample being tested. The light energy is produced by a fluorescer which is integrated into support bodies in the form of beads or other structures. The support bodies are coated with a ligand that is capable of specifically binding to the organic material or reactant of interest. When the present invention is used as a direct assay, the reactant is radiolabeled. Then, the sample containing the radiolabeled reactant is mixed in an aqueous solution with the support bodies, causing the reactant to bind to the ligand. This places the radiolabeled reactant in close enough physical proximity to the support bodies to cause the radiation energy emitted from the radiolabeled reactant to activate the fluorescer integrated into the support bodies, thereby causing the fluorescer to emit light energy. The level of the light energy produced is related to the amount of reactant that is bound to the ligand, which in turn, is indicative of the amount of reactant present in the sample being tested.

The present invention may also be utilized as a competitive assay to determine the amount of a reactant contained in a sample. In this situation, a known amount of the reactant is radiolabeled. The reactant of interest in the sample being tested remains unlabeled. Both the labeled and unlabeled reactant are capable of specifically binding with the ligand. In the assay process, both the labeled and unlabeled organic materials are placed in an aqueous solution, together with the support bodies that have been impregnated with the fluorescer and coated with the ligand. Since the ligand does not favor either the labeled or unlabeled reactant, the reactants bind to the ligand in proportion to their relative amounts present in the aqueous solution. However, only the radiolabeled reactant that binds to the ligand is brought in close enough proximity to the support bodies to cause the radiation energy emitted thereby to activate the fluorescer integrated into the support bodies. Thus, the level of light energy produced by the fluorescer is inversely proportional to the quantity of unlabeled reactant present in the sample.

In both the direct and competitive assays, radiation energy emitted by the radiolabeled reactant, which is capable of activating the fluorescer, has a limited range of travel in water. Thus, the reactant that has not bound to the ligand is too far away from the support structures to permit the radiation energy emitted therefrom to reach the fluorescer. Thus, since only the radiolabeled reactant that actually binds to the ligand is responsible for causing the fluorescer to emit light energy, the radioactive reactant that has not bound to the ligand need not be separated from the ligand-reactant complex prior to measuring the level of light energy emitted by the fluorescer. Thereby, as a consequence of the present invention, the laborious and time-consuming procedure of separating the unbound labeled reactant from the bound complexes by centrifuge, precipitation, washing and other procedures is eliminated, as are the large quantities of radioactive waste material produced by these separation techniques.

In a further aspect of the present invention, a unique technique is provided for integrating the fluorescer into the support bodies. Initially, the support bodies are soaked in a solvent for the fluorescer which is miscible in water to dehydrate the bodies. Thereafter, the bodies are placed in a solution composed of the fluorescer and solvent so that the fluorescer is integrated and/or adsorbed into the bodies. Then, the bodies are removed from the solvent and then placed in an aqueous solution which causes precipitation of the fluorescer within the bodies, thereby locking the fluorescer therein. By this technique, the fluorescer is integrated within the interior of the bodies so that the radiolabeled reactant is placed in very close proximity to the fluorescer upon binding to the ligand, which is disposed on the exterior of the bodies.

DETAILED DESCRIPTION

Figure 1:
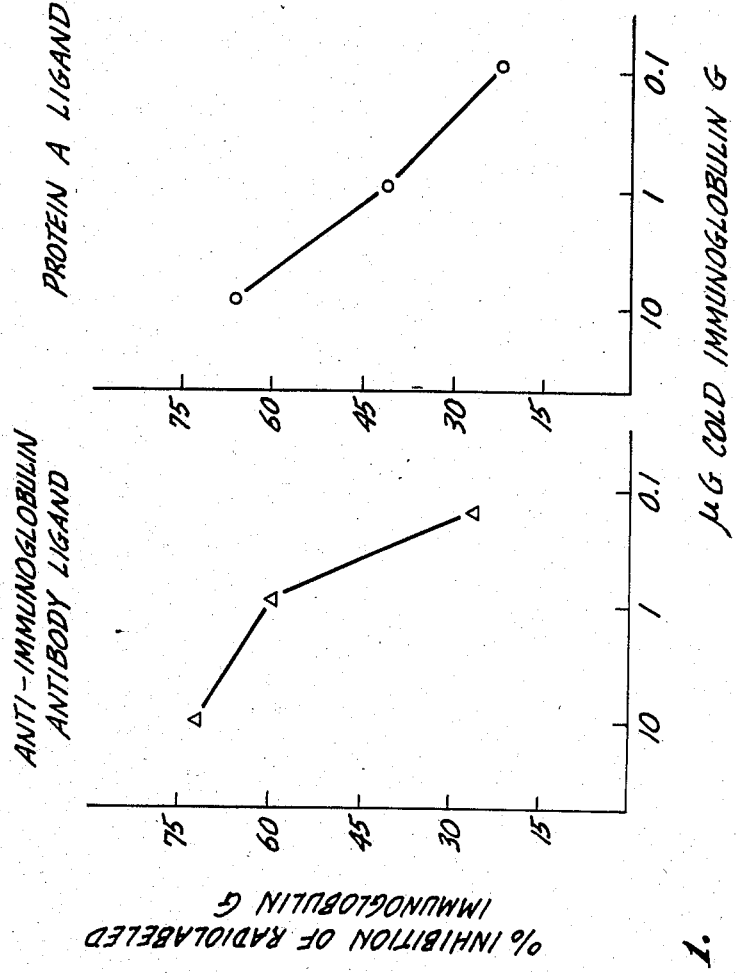

In accordance with the present invention, support bodies or particles in the form of beads or other structures are impregnated and/or coated with a material capable of fluorescence when excited by radioactive energy. The beads are coated with a ligand that is capable of specifically binding to a reactant of interest by covalently linking or directly attaching the ligand to the beads. The beads are then mixed in a water-based solution containing the reactant that has been radiolabeled. Upon binding of the radiolabeled reactant to the ligand, the fluorescer integrated into the beads is placed in close enough physical relationship to the reactant to allow the radiation energy emitted from the reactant to activate the fluorescer thereby causing the fluorescer to emit light energy. The level of light energy emitted, which is indicative of the extent to which the ligand is bound to its reactant, may be conveniently measured with a scintillation counter or other monitoring device employing a photomultiplier tube.

The radiation energy emitted by the radiolabeled reactant molecules has a very limited range of travel in water. The reactant molecules that have not bound to the ligand are, for the most part, located too far away from the ligand to enable the radiation energy emitted from these unbound reactant molecules to reach the fluorescer in the support structure, i.e., beads. Since there is very little likelihood of chance excitation of the fluorescer by the radioactive energy of these unbound reactant molecules, the reactant molecules that have not bound to the ligand need not be separated from the ligand-reactant complexes prior to scintillation counting of the light energy emitted by the fluorescer excited by radioactive energy from the reactant molecules that have bound to the ligand. Thus, the traditional laborious and potentially hazardous procedure of separating the unbound reactant from the ligand-reactant complexes is eliminated.

The present invention may also be used in conjunction with a competitive assay procedure. In this instance, the support bodies, having a fluorescer integrated therein and coated with an appropriate ligand, are placed in an aqueous solution containing a known quantity of radiolabeled reactant and a sample containing an unknown amount of the same, but unlabeled reactant. Since the ligand does not favor binding to either the labeled or unlabeled reactant over the other, the amount of labeled reactant binding to the ligand will be inversely proportional to the quantity of unlabeled reactant present in the sample. Prior to the assaying of a particular sample, different known amounts of unlabeled reactant are mixed together in individual vials with constant amounts of radiolabeled reactant and with a fixed quantity of ligand coated beads. The level of fluorescent energy generated by excitation of the fluorescer from the radiolabeled reactant that has bound to the ligand is measured for each vial containing a known amount of the unlabeled reactant. From the results of these measurements, a standard curve may be prepared depicting the level of fluorescent energy measured per quantity of unlabeled reactant present. Then, when a particular sample containing an unknown amount of unlabeled reactant is assayed, the concentration of the unlabeled reactant in the sample may be determined from the standard curve once the level of fluorescent energy being emitted is measured.

As in the direct assay procedure described above, in the competitive assay, only the radiolabeled reactant molecules that are bound to the ligand are in close enough proximity to the beads to allow the radiation energy emitted by the labeled reactant to bombard the fluorescer integrated into the beads. The detected level of fluorescent energy, therefore, is a reflection of the proportion of the radiolabeled reactant which actually binds to the ligand. As a consequence, there is no need to wash the beads or otherwise attempt to remove the unbound radioactive reactant from the ligand; instead, the level of fluorescent energy may be measured with all of the components of the assay still present in the vial. Moreover, the time required to complete the assay is limited only by the ligand-reactant binding reaction rate of the system under investigation.

As noted above, the ligand is bonded to and the fluorescer is integrated with a structural support, such as beads. Various types of beads may be utilized, such as polyacrylamide, acrylamide, agarose, polystyrene, polypropylene, polycarbonate or Sepharose 4B beads (from Pharmacia Fine Chemicals, Uppsala, Sweden). The present invention also may be carried out with other shapes or types of support structures, for instance latex particles, as long as the ligand molecules can be covalently or otherwise attached thereto and a fluorescer integrated therewith.

Beads, such as the Sepharose 4B beads noted above, are commercially available in an activated state. Compounds, such as cyanogen bromide, are incorporated in the beads to covalently bind with certain ligands. The process by which the ligand is bound to the beads is dependent on the type of bead and the particular ligand employed. For instance, for Sepharose 4B beads activated with cyanogen-bromide, a ligand in the form of Staphylococcus aureus protein A or an antibody to a specific reactant may be bound to the beads by placing the beads in a solution containing the protein A or antibody and an appropriate buffer. Thereafter, the excess protein A or antibody is washed away and the remaining active sites on the beads to which no protein A or antibody had attached are blocked with an appropriate blocking agent, such as glycine. This prevents the reactant of interest and others from binding directly to the beads, rather than to the ligand. Other techniques for bonding a ligand to beads include the use of carbodiimide coupler, tannic acid, glutaraldehyde and polyethylene glycol.

As noted above, in accordance with the present invention, a fluorescer is integrated within the beads to give off light energy when radiolabeled reactant is brought in close enough proximity to the fluorescer to cause excitation thereof, i.e., by binding to the ligand on the bead surface. Various types of fluorescers may be used; however, since the process of the present invention takes place in an aqueous solution, the fluorescer must be insoluble in water so that it does not dissociate from the beads during the assay procedure. Also, the fluorescer employed must be excitable to a higher energy state by the particular wavelength of the radioactive energy rays emitted by the radiolabeled reactant, and also must release sufficient light energy when returning to its normal energy state to be detected by a scintillation counter or other detection device utilizing a photomultiplier tube. An example of a fluorescer that has been found to meet these requirements for use with radioactive energy in the form of beta rays or auger electrons is diphenyloxazole (hereinafter "PPO").

The present invention involves a novel process for integrating a fluorescer into a support structure, such as beads. Since the fluorescer is insoluble in water, an appropriate transfer medium, in which the fluorescer is soluble, must be used to incorporate the fluorescer into the beads. Moreover, the transfer medium itself must be miscible with water.

The novel method of the present invention for integrating the fluorescer into the beads includes soaking the beads in an appropriate transfer solvent for the fluorescer that is miscible with water thereby to dehydrate the beads. Thereafter, the beads are incubated in a solution of the fluorescer and solvent. The fluorescer, which is in solution, is absorbed into the bead. The excess solvent is then discarded and the fluorescer is precipitated, adsorbed and/or integrated inside the bead by adding water or a buffered saline solution. Precipitating the fluorescer within the beads locks the fluorescer therein. Next, the beads are washed to remove the excess precipitated fluorescer and then resuspended in a solution containing both a detergent, such as Tween 20, to prevent the beads from sticking together and gelatin to bind to any sites on the surface of the beads that either have not been blocked by the previously employed blocking solution or bound to a ligand. This lowers the nonspecific binding tendency of the beads. Finally, a bactericide, such as sodium azide, can be applied to the beads to prevent the growth of bacteria thereon.

Applicant has found the dimethyl sulfoxide (hereinafter "DMSO") may be utilized as a transferring solvent if PPO is used as a fluor. PPO is soluble in DMSO, and DMSO is miscible in water. Also, the DMSO does not hinder the ability of the PPO to precipitate within the beads when subjected to an aqueous solution.

The process of the present invention requires the use of radio-labeled reactants. The radiolabeled reactants are biologically and chemically identical to an unlabeled reactant, with the exception that the labeled reactants emit radioactive energy due to the decaying of the radioactive isotope present.

The technique used for labeling of the reactant varies with the type of radioactive isotope employed. For instance, labeling can be accomplished by replacing one of the atoms of the reactant molecules with a corresponding radioactive isotope. A hydrogen atom could be replaced with: tritium, $^3H$; a carbon atom replaced with carbon-14, $^{14}C$; or a strontium atom replaced with strontium-38, $^{38}Sr$. In another labeling process, rather than replacing the atoms of the reactant with a radioactive isotope, an isotope may be added to the reactant molecule. Such radioactive isotopes in common use include: iodine-125, $^{125}I$; and iron-59, $^{59}Fe$. In situations in which biological organisms or parts of those organisms are capable of synthesizing proteins, labeling can be carried out by culturing the organism with an appropriate radiolabeled precurser, such as methionine-35 ($^{35}S$), to cause the organism to incorporate the isotope into its products. Many reactants, such as antigens, antibodies, hormones, hormone receptors, enzymes, or enzyme cofactors, are readily available in radiolabeled form from various commercial sources.

Radioactive isotopes used to label the reactant have only a limited range in water so that, for the most part, only the radioactive energy from the labeled reactant that binds to the ligand actually activates the fluorescer. If PPO is used as a fluorescer, applicant has found that isotopes that emit either beta rays or auger electrons from gamma ray emissions fulfill this requirement. PPO does not fluoresce from the gamma rays themselves which have a longer range of travel than beta rays or auger electrons.

The assay process of the present invention may be utilized in conjunction with any ligand-reactant combination or system that specifically binds together and in which the reactant may be radiolabeled without affecting its specificity for the ligand. Examples of such ligand-reactant combinations include antibodies and their corresponding antigens. Either the antibody or antigen may be attached to the bead or other type of support structure to function as the ligand, with the corresponding antigen or antibody serving as the reactant. Another ligand-reactant system may be composed of protein A and corresponding immunoglobulins. The need to ascertain the presence of antigens, antibodies, and immunoglobulins exists in many clinical and research settings, especially in the detection of diseases and allergies and in investigations of the immune system.

Additional ligand-reactant systems with which the present invention is especially useful include: (1) lectins-glycoproteins; (2) biotin-avidin; (3) hormone receptor-hormone; (4) enzyme-substrate or cofactor; (5) RNA-DNA; and (6) DNA-DNA. It is to be understood that in the present invention either element may serve as the ligand or reactant.

The present invention also may be of particular value in conducting enzyme kinetic strudies. The enzyme may serve as a ligand to bind with the radiolabeled reactant. Since all of the reagents of the assay system are always present together in the same vial and because the reagents are suspended in an aqueous-based buffer rather than an organic solvent, kinetic experiments may be conveniently carried out by simply measuring the light energy emitted from the same vial at different time intervals to determine the reaction rate of the reagents. Also, in the RNA-DNA system, the commonly used Northern, Southern and Western Blot tests may be advantageously replaced with the assay of the present invention.

EXAMPLE I

Immunoglobulin-G Direct Detection Assay With Tritium Labeling

To use the assay of the present invention to detect the presence of immunoglobulin-G, cyanogen-bromide activated Sepharose 4B beads (obtained from Pharmacia Fine Chemicals, Uppsala, Sweden) are covalently coated with Staphyloccus aureus cowan strain 1 protein A (Pharmacia Fine Chemicals, Uppsala, Sweden) or with anti-immunoglobulin-G antibody. This is accomplished by swelling and washing one gram of cyanogen-bromide activated Sepharose 4B beads in one millimolar hydrochloric acid. Then, two milliliters of the washed beads are placed in a solution composed of either two milligrams of protein A or 15 milligrams of the immunoglobulin-G fraction of a rabbit antiserum to the human immunoglobulin-G heavy chain, together with sodium bicarbonate buffer, pH 8.3, containing 0.5 molar saline. The suspension is incubated for two hours at room temperature and then the excess protein is washed away by centrifuging. Thereafter, the remaining active sites on the beads are blocked with 0.2 molar glycine. The beads are next washed with acetate buffer and bicarbonate buffer.

A fluorescer in the form of PPO is next incorporated into the beads. This is accomplished by dehydrating the coated beads by soaking them in DMSO for 15 minutes to remove any water in the beads that would cause premature precipitation of the PPO since PPO is insoluble in water. This step is repeated twice more and then the excess solvent removed by sedimentation. The beads are next incubated for 30 minutes at room temperature in a 20 to 40 percent weight by volume solution of PPO in DMSO. After incubation, the excess solution is discarded and the PPO precipitated inside the beads by adding ten volumes of either phosphate buffered saline (hereinafter "PBS") or water. The suspension is then washed five times in PBS to remove the excess precipitated PPO which is not bound inside the beads. Thereafter, the beads are resuspended at a final concentration of ten percent volume/volume in PBS supplemented with 0.5 percent volume/volume Tween 20 as a detergent to help prevent the beads from sticking together and 0.1 percent weight/volume gelatin to bind to the remaining sites on the beads which were not blocked by reaction with protein A, immunoglobulin-G antibody or the glycine. This minimizes any nonspecific binding of radiolabeled reactant to the beads. Lastly, sodium azide, $NaN_3$ in an amount of 0.01 percent weight/volume, can be added to prevent bacterial growth.

In a direct assay for immunoglobulin-G, 50 microliters of the protein A or anti-immunoglobulin-G antibody coated beads are mixed together in scintillation vials with various concentrations of immunoglobulin-G labeled to a specific activity of $5 \times 10^{12}$ counts per minute per millimole with $^3H$-acetic anhydride. PBS supplemented with 0.5 percent volume/volume Tween is added to the vials to bring the total volume in each vial up to a total of 3.0 milliliters. Then, the light energy produced by the bombardment of the PPO with the beta rays from the radiolabeled immunoglobulin-G is directly measured by a scintillation counter. The results of the assay wherein beads coated with protein A were utilized, shown in Table I, indicate that increasingly higher counts per minute were obtained by increasing the concentration of tritium-labeled immunoglobulin-G in the sample. PPO-impregnated Sepharose 4B beads that were not coated with either a protein or anti-immunoglobulin-G antibody were used as a control, as also shown in Table I.

TABLE I

DIRECT DETECTION ASSAY FOR HUMAN IMMUNOGLOBULIN-G

| Bead Source | Tritium Labeled Human Immunoglobulin-G (Micrograms) | Counts Per Minute Determined After 5 Minute Incubation |
|---|---|---|
| 50 Microliters of PPO Integrated Sepharose 4B Beads Coated with protein A | 5 | 4221 |
| | 10 | 5375 |
| | 20 | 6140 |
| | 40 | 7286 |
| 50 Microliters of PPO Integrated uncoated Sepharose 4B Beads | 40 | 35 |

EXAMPLE II

Immunoglobulin-G Direct Detection Assay With Iodine 125

This Example is identical with Example I, except that the protein A or anti-immunoglobulin-G antibody coated beads were mixed with various concentrations of human immunoglobulin-G labeled with $^{125}I$ to a specific activity of $8 \times 10^4$ counts per minute per millimolar by the Chloramine T method. The protein A or anti-immunoglobulin-G antibody coated beads were placed in scintillation vials with various concentrations of $^{125}I$ labeled human immunoglobulin-G and then the vials were placed directly into a scintillation counter to measure the resulting level of photon emission. The results of these tests are shown in Table II for 5-minute and 60-minute incubation periods. These data confirm that the assay can be measured immediately after mixing labeled reactant with PPO-impregnated ligand bound beads.

TABLE II

DIRECT DETECTION ASSAY FOR HUMAN IMMUNOGLOBULIN-G

| Bead Source | Iodine-125 Labeled Human Immunoglobulin-G | Counts Per Minute Determined After 5 min/60 min Incubations |
|---|---|---|
| 75 Microliters of PPO Integrated Sepharose 4B Beads Coated with protein A | 125 ng | 10596/10238 |
| | 375 ng | 14880/14910 |
| | 500 ng | 18132/19638 |
| | 750 ng | 26216/27640 |
| | 1000 ng | 33876/37784 |
| | 1500 ng | 40066/41846 |
| 75 Microliters of PPO Integrated Sepharose 4B Beads Coated with anti-immunoglobulin-G antibody | 125 ng | 11030/11874 |
| | 375 ng | 16762/18198 |
| | 500 ng | 22684/24985 |
| | 750 ng | 24088/25946 |
| | 1000 ng | 25904/31514 |
| | 1500 ng | 30056/37068 |

EXAMPLE III

Competitive Assay for Immunoglobulin-G

Cyanogen-bromide activated Sepharose 4B beads (Pharmacia Fine Chemicals, Uppsala, Sweden) are coated with either protein A (0.1 milligrams per milliliter of gel) or anti-immunoglobulin-G antibody (1.5 milligrams per milliliter of gel) in the manner set forth in Example I. Also, the Sepharose 4B beads are impregnated with the fluorescer PPO in the manner discussed in Example I. Fifty-microliter quantities of the prepared beads are mixed together in scintillation vials with 0.5 micrograms of $^{125}I$-human immunoglobulin-G and increasing concentrations of unlabeled human immunoglobulin-G. The samples are then brought up to three milliliters each by adding PBS supplemented with 0.5 percent volume/volume of Tween. The sample is then immediately counted for photon emission levels.

From the photon emission level measurements, standard inhibition curves were plotted in terms of the percent of inhibition of binding of the radiolabeled immunoglobulin-G caused by different quantities of unlabeled immunoglobulin-G. The inhibition curves using both anti-immunoglobulin-G antibody and protein A as ligands shown in FIG. 1. A sample containing an unknown amount of immunoglobulin-G can now be measured for percent of inhibition of the radiolabeled reactant and from this measurement the quantity of immunoglobulin-G present can be determined by using FIG. 1.

EXAMPLE IV

Thyroxin Determination

This Example involves the use of the present invention to develop a standard inhibition curve for the detection of thyroxin. Cyanogen-bromide activated Sepharose 4B beads were coated with protein A and then impregnated with PPO in the manner described in Example I. Two hundred microliters of the prepared beads were pipetted into individual scintillation vials together with 400 microliters of a rabbit anti-thyroxin antiserum (obtained from Abbott Laboratories, Chicago, IL).

Figure 2:
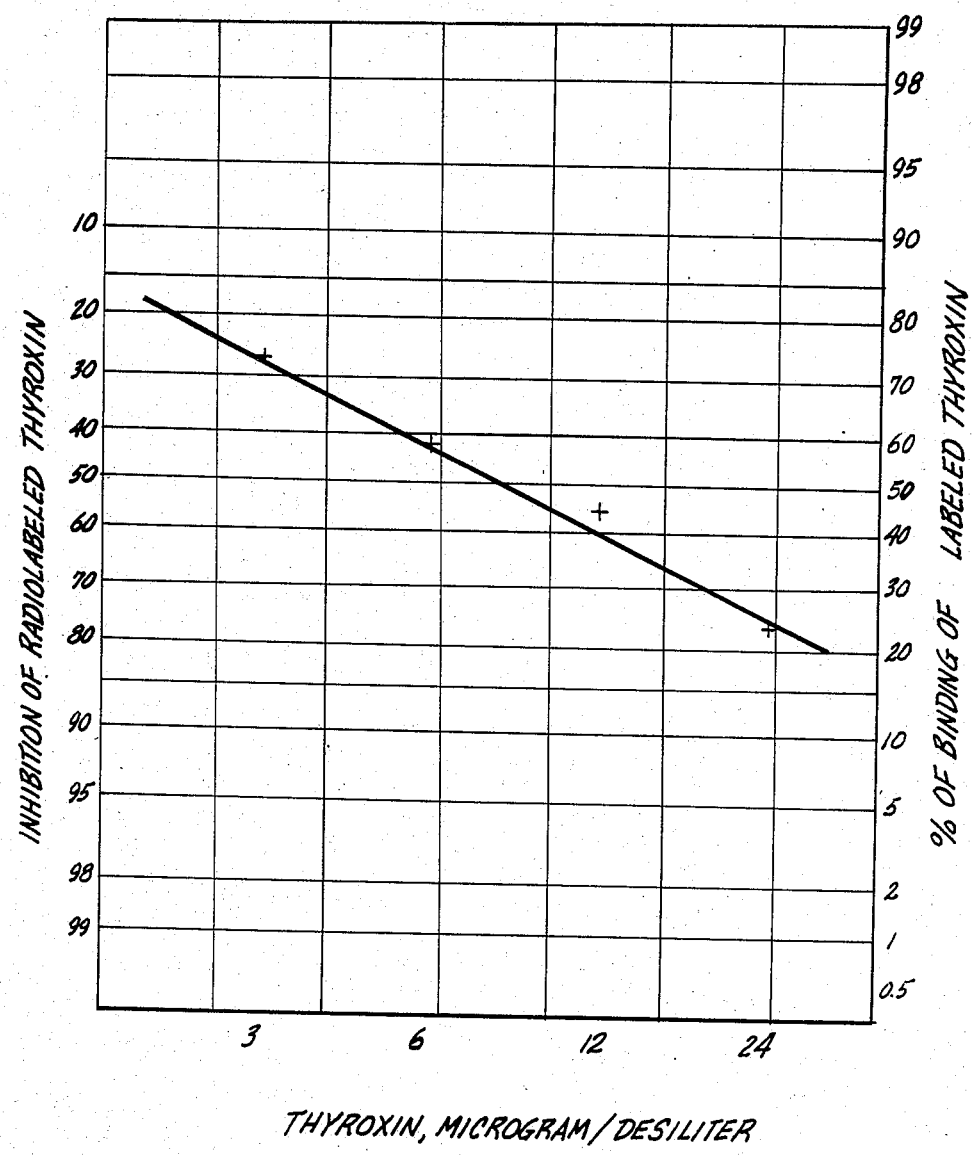

Twenty-five microliters of various concentrations of unlabeled thyroxin (obtained from Abbott Laboratories, Chicago, IL) were added to each vial. Next, 100 microliters of thyroxin labeled with the isotope iodine-125 (obtained from Abbott Laboratories, Chicago, IL) were added to the vials. Lastly, the volume of the reaction mixture in each vial was brought up to three milliliters by the addition of PBS supplemented with 0.5 percent volume/volume of Tween. The photon emission level in each vial was then measured in a scintillation counter and the results plotted in FIG. 2 on a probability-log format. As shown in FIG. 2, as the volume of unlabeled thyroxin added to the vials increased, the proportion of labeled thyroxin that bound to the beads decreased as expected. This standard inhibition curve can be used to determine the amount of thyroxin present in an unknown sample by using the same protocol described above in Example III to determine the percent of radiolabeled thyroxin that is inhibited from binding on the beads. From this value, the amount of thyroxin present in the sample may be conveniently read from the curve.

As will be apparent to those skilled in the art to which the invention is addressed, the present invention may be embodied in forms other than those specifically disclosed above without departing from the spirit or essential characteristics of the invention. The particular embodiments of the immediate ligand detection assay method, described above, are therefore to be considered in all respects as illustrative and not restrictive. The scope of the present invention is as set forth in the appended claims rather than being limited to the examples of the immediate ligand detection method set forth in the foregoing description.

The embodiments of the invention in which an exclusive property or privilege is claimed are defined as follows:

1. An immediate ligand detection process, comprising:
   (a) placing in an aqueous suspension a plurality of support particles impregnated with a fluorescer and to which ligands have been attached;
   (b) adding to the suspension fluid a radiolabeled sample reactant capable of specifically biochemically binding to the ligand, said radiolabeled sample reactant emitting radiation energy capable of activating the fluorescer, upon the binding of the sample reactant to the ligand, the sample reactant is disposed in close enough proximity to the support particles to cause the radition energy from the sample reactant to activate the fluorescer to produce light energy, whereas the sample reactant that does not bind to the ligand is generally too far removed from the support particles to enable the radioactive energy to activate the fluorescer; and
   (c) measuring the light energy emitted by the fluorescer with the entire quantities of the support particles and radiolabeled sample reactant remaining together in aqueous suspension.

2. The process of claim 1, wherein the fluorescer is insoluble in water.

3. The process of claim 2, wherein the fluorescer is diphenyloxazole.

4. The process of claim 2, further including impregnating the support particles with a fluorescer by:
   (a) placing the fluorescer in solution in a solvent that is miscible in water;
   (b) adding support particles to the solution, said support particles being porous to the solution;
   (c) removing the support particles from the solution; and
   (d) exposing the support particles to water to precipitate the fluorescer impregnated therein.

5. The process of claim 4, wherein the fluorescer is diphenyloxazole.

6. The process of claim 5, wherein the solvent is dimethyl sulfoxide.

7. The process of claim 4 further including the step of dehydrating the support particles by soaking them in the solvent before adding them to the solution.

8. The process of claim 1, wherein the sample reactant is labeled with beta ray or auger electron producing radioactive material.

9. A competitive immediate ligand detection assay process, comprising:
   combining together in an aqueous medium:
      a sample to be assayed containing an unknown amount of cold ligand reactant;
      a known quantity of radiolabeled ligand reactant; and
      a plurality of support particles having fluorescer integrated therewith capable of emitting photons when activated by the radiation energy emitted by the radiolabeled ligand and having ligand attached to the outer surface thereto, said ligand capable of indiscriminately binding with both said cold and radiolabeled ligand reactant whereupon the binding of the ligand with the radiolabeled ligand reactant positions the radiolabeled ligand reactant close enough to the support particles to activate the fluorescer to emit photons through the aqueous medium, whereas the unbound radiolabeled ligand reactant is generally positioned too far away from the support particles to enable the radioactive energy emitted thereby to activate the fluorescer; and
   measuring the photons emitted by the fluorescer with the entire quantities of cold ligand reactant containing sample, radiolabeled ligand reactant and support particles remaining combined together in the aqueous medium.

10. The assay of claim 9, wherein the fluorescer is insoluble in water.

11. The assay of claim 10, wherein the fluorescer includes diphenyloxazole.

12. The assay of claim 10 further including integrating the fluorescer with the support particles by:
   (a) placing the fluorescer in solution in a solvent that is miscible in water;
   (b) adding the support particles to the solution, said support particles being porous to the solution;
   (c) removing the support particles from the solution; and
   (d) exposing the support particles to water to precipitate the fluorescer integrated with the support particles.

13. The assay of claim 12, wherein the fluorescer includes diphenyloxazole.

14. The assay of claim 13, wherein the solvent includes dimethyl sulfoxide.

15. The assay of claim 12, further including the step of dehydrating the support particles by soaking them in the solvent before adding the particles to the solution.

* * * * *